US010271962B2

(12) United States Patent
Heald et al.

(10) Patent No.: US 10,271,962 B2
(45) Date of Patent: Apr. 30, 2019

(54) BONE GRAFT DISPENSING DEVICE

(71) Applicants: Robert Heald, Shorewood, IL (US); Richard Lim, Burr Ridge, IL (US)

(72) Inventors: Robert Heald, Shorewood, IL (US); Richard Lim, Burr Ridge, IL (US)

(*) Notice: Subject to any disclaimer, the term of this patent is extended or adjusted under 35 U.S.C. 154(b) by 1 day.

(21) Appl. No.: 15/810,303

(22) Filed: Nov. 13, 2017

(65) Prior Publication Data

US 2018/0133027 A1   May 17, 2018

Related U.S. Application Data

(60) Provisional application No. 62/422,979, filed on Nov. 16, 2016.

(51) Int. Cl.
*A61F 2/46* (2006.01)
*A61L 27/54* (2006.01)
*A61F 2/30* (2006.01)
*A61F 2/28* (2006.01)

(52) U.S. Cl.
CPC .......... *A61F 2/4601* (2013.01); *A61F 2/4603* (2013.01); *A61L 27/54* (2013.01); *A61F 2/30723* (2013.01); *A61F 2002/2817* (2013.01); *A61F 2002/2835* (2013.01)

(58) Field of Classification Search
CPC ............ A61B 17/8802; A61B 17/8805; A61B 17/8811; A61B 17/8816; A61B 17/8819; A61B 17/8822; A61B 17/8825; A61F 2/4601
USPC ................ 606/92–95, 108; 623/17.11–17.16
See application file for complete search history.

(56) References Cited

U.S. PATENT DOCUMENTS

| 3,353,718 A * | 11/1967 | McLay ............. A61M 5/31586 222/158 |
| 6,793,660 B2 * | 9/2004 | Kerr ................... A61B 17/3472 606/92 |
| 2002/0026197 A1 * | 2/2002 | Foley ................... A61B 17/025 606/105 |

* cited by examiner

*Primary Examiner* — Julianna N Harvey
*Assistant Examiner* — Christina Negrellirodrigue
(74) *Attorney, Agent, or Firm* — Richards Patent Law P.C.

(57) ABSTRACT

The present disclosure provides a device and method for applying a bone graft material to the body. The device includes a cylinder into which bone graft material is loaded. Specifically, the bone graft material is loaded into the cylinder through a funnel at a proximal end of the cylinder and dispensed through a tip at a distal end of the cylinder. After the bone graft material is loaded, a sleeve within the cylinder can be removed in order to create a channel within the bone graft material. Water or other hydrating fluid may be inserted into the channel through a port adjacent the proximal end of the cylinder in order to hydrate the bone graft material.

6 Claims, 7 Drawing Sheets

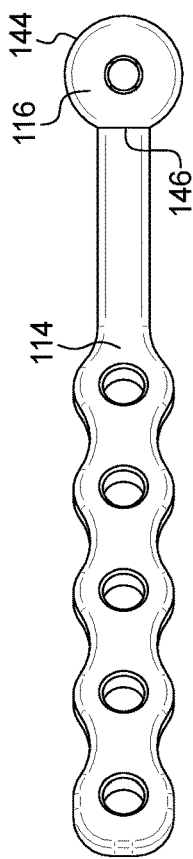
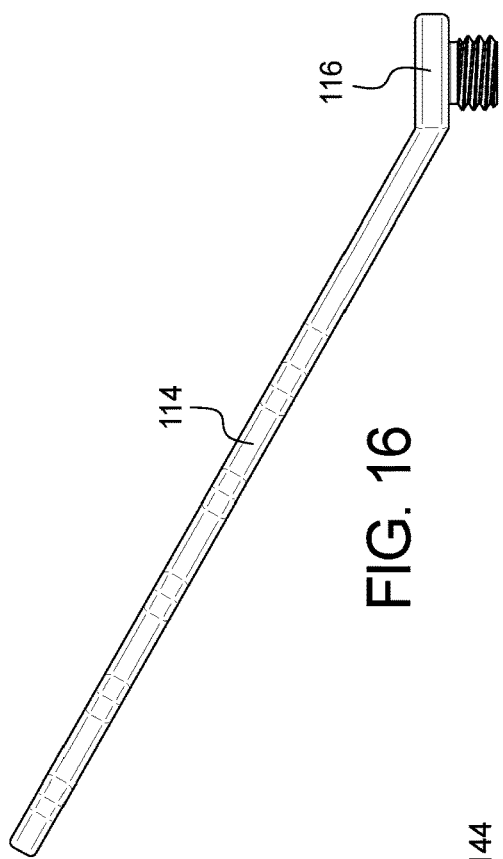
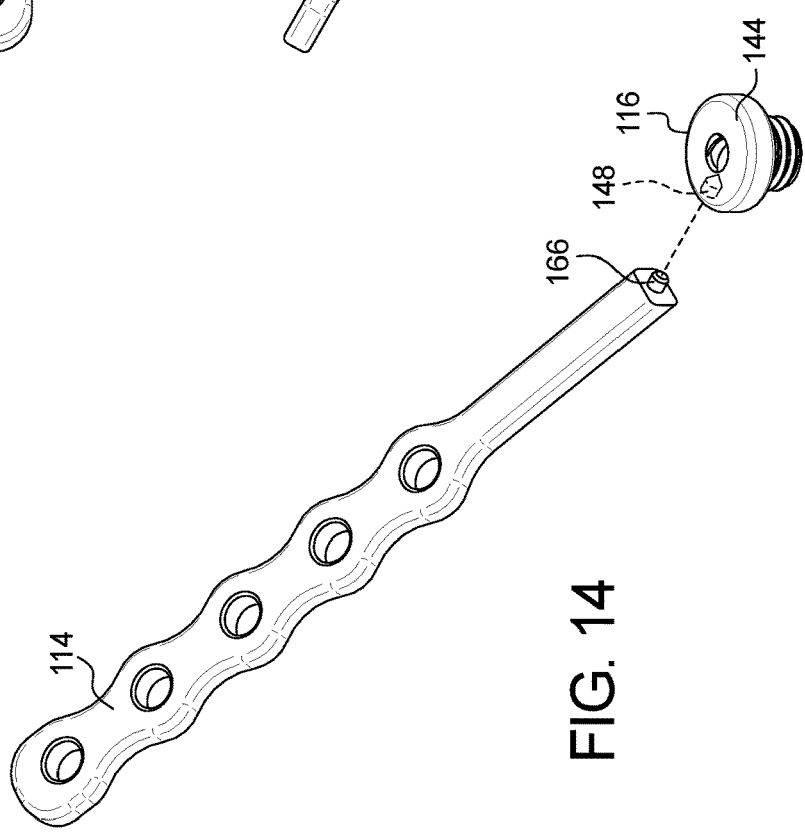

BONE GRAFT DISPENSING DEVICE

CROSS-REFERENCE TO RELATED APPLICATIONS

This application incorporates by reference and claims the benefit of priority to U.S. Provisional Application 62/422,979 filed on Nov. 16, 2016.

BACKGROUND OF THE INVENTION

The present subject matter relates generally to devices and methods for dispensing bone graft material or similar components.

During surgical procedures, a bone graft dispensing device is used to insert a bone graft material into open fractures or wounds. The bone graft material may include any bone graft substitute, including allograft, autograft, and synthetic bone graft material, and is often a thick, putty-like material. Conventional bone graft dispensing devices include a plunger that is advanced through a cylinder to dispense the bone graft material through a tip.

However, conventional bone graft dispensing devices are often difficult to manipulate during use. The bone graft material is typically sticky and difficult to handle as it is loaded into and advanced through a bone graft dispensing device. To move the plunger through the cylinder, the plunger must be connected to a hand or motor powered drill that rotates the plunger as it moves through the cylinder. Each of these actions of manipulating the device occur as the bone graft material is being applied to the patient during surgery.

The positioning of the tip of the device in the surgical area of the patient is critical, particularly when operating in areas with small bones such as the spine, areas that are highly sensitive, or procedures that involve hardware components to temporarily or permanently align bones while surgery heals. The difficulty in manipulating the device during surgery can lead to bone graft material dispensed in the incorrect area as well as unintentionally striking the surgical area of the patient with the device.

Accordingly, there is a need for a bone graft dispensing device that is easy to use, minimizes the likelihood of the device striking the patient, and hydrates bone graft material as it moves through the device.

BRIEF SUMMARY OF THE INVENTION

To meet these needs and others, the present disclosure provides a device and method for applying a bone graft material to the body. The device includes a cylinder into which bone graft material is loaded. Specifically, the bone graft material is loaded into the cylinder through a funnel at a proximal end of the cylinder and dispensed through a tip at a distal end of the cylinder. The distal end of the cylinder also includes a protrusion extending outwardly from a central axis of the cylinder to prevent the device from unintentionally striking or contacting the surgical area of the patient.

Water or other hydrating fluid may be inserted into the cylinder through a port adjacent the proximal end of the cylinder in order to hydrate the bone graft material. After the bone graft material is loaded, the sleeve is removed in order to create a channel within the bone graft material prior to being dispensed from the device. Liquid injected into the device through the port travels through the channel and hydrates the bone graft material throughout the length of the cylinder.

The device can include a plunger that is moveable within the cylinder and pushes the bone graft material to the tip. A cap is threaded onto the funnel at the proximal end of the cylinder, and a handle extends outwardly from the cap. Specifically, the handle includes a grip end where the user grasps the device and a connection end that engages with the cap. The cap includes a threaded portion extending from a cover that is received within and screws into the funnel so that the cover encloses the funnel.

The plunger can be a threaded graft impactor that rotates through the handle to advance the bone graft material. As a distal end of the plunger is threaded into the cylinder, the proximal end of the plunger includes an adapter that may cooperate with a handle or a powered drill.

During use, a user can load the bone graft material into the funnel of the cylinder. The user can insert the distal end of the plunger into the funnel and, using a manual or powered drill, rotates the plunger through the cylinder, causing the bone graft material to dispense from the tip. The user may also attach a syringe loaded with a hydrating liquid to the port of the cylinder and inject the hydrating liquid to hydrate the bone graft material as it moves through the cylinder.

One objective of the present application is to provide a device that prevents or minimizes impact on the surgical area of the patient.

Another advantage of the device is the simplified and easy loading of the device with the bone graft material so as to minimize any disturbance on the positioning of the tip of the device during use.

Additional objects, advantages and novel features of the examples will be set forth in part in the description, and in part will become apparent to those skilled in the art upon examination of the following description and the accompanying drawings or may be learned by production or operation of the examples. The objects and advantages of the concepts may be realized and attained by means of the methodologies, instrumentalities and combinations described herein.

BRIEF DESCRIPTION OF THE DRAWINGS

FIG. 14 an exploded, perspective view of the handle and the cap of the bone graft dispensing device.

FIGS. 15 and 16 are top and side elevational views, respectively, of the handle and cap.

DETAILED DESCRIPTION OF THE INVENTION

Figure 1:
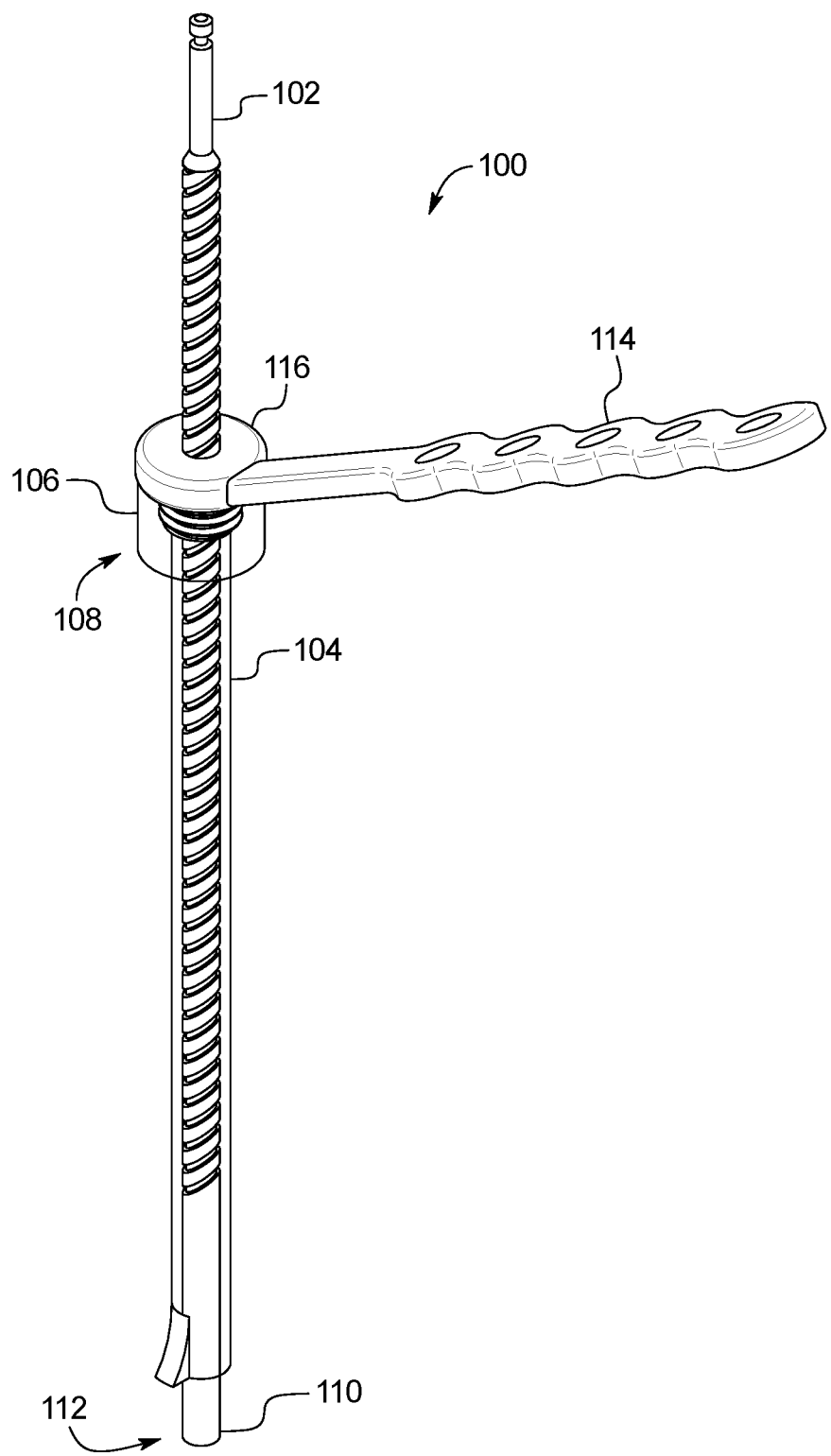
FIG. 1 is a perspective view of an example of the bone graft dispensing device of the present application.

The present disclosure provides a device 100 and method for applying a bone graft material to the body. The device 100 includes a cylinder 104 into which bone graft material is loaded. The bone graft material includes, but is not limited to, _____.

The bone graft material can be loaded into the cylinder through a funnel 106 at a proximal end 108 of the cylinder 104 and dispensed through a tip 110 at a distal end 112 of the cylinder 104. The device can include a plunger 102 that can move axially through a cylinder 104 along a central axis 135 to move the bone graft material through the cylinder and out of the tip 110. The distal end of the cylinder can include a protrusion extending outwardly from a central axis of the cylinder to prevent the device from unintentionally striking or contacting the surgical area of the patient.

Figure 3:
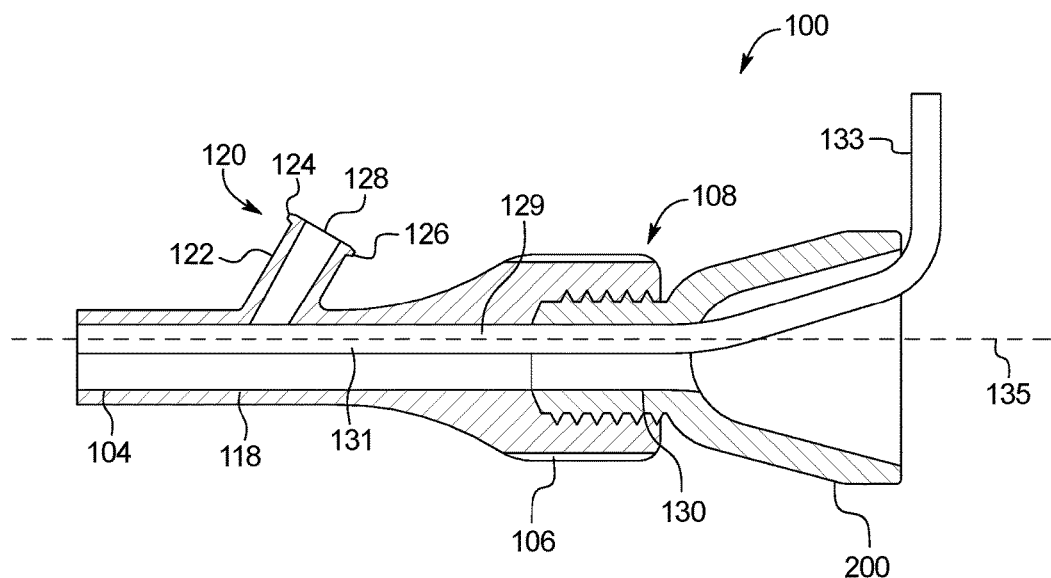
FIG. 3 is an enlarged view of the sleeve within the funnel of the bone graft dispensing device of FIG. 29.
Figure 4:
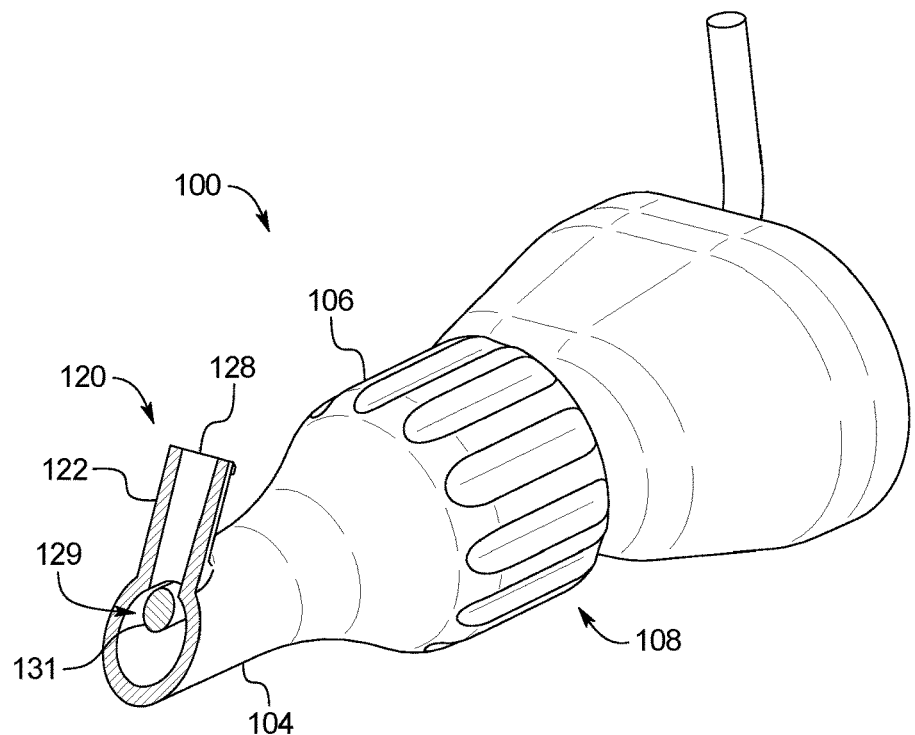
FIG. 4 is a perspective, sectional view of the bone graft dispensing device generally taken along lines 31-31 of FIG. 29.
Figure 5:
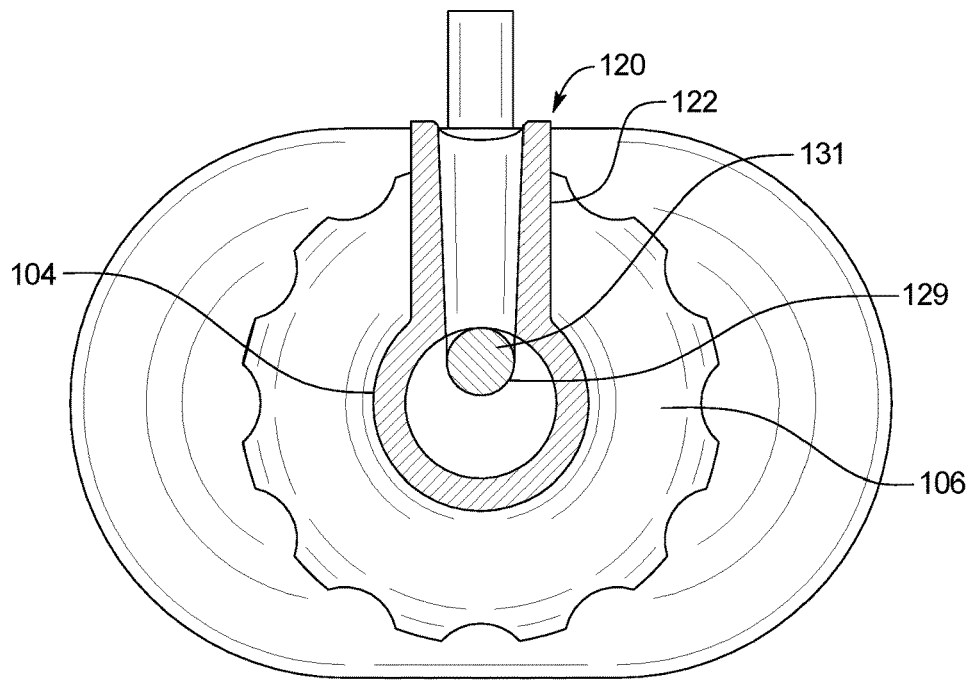
FIG. 5 is a front elevational, sectional view of the of the bone graft dispensing device generally taken along lines 31-31 of FIG. 29.
Figure 6:
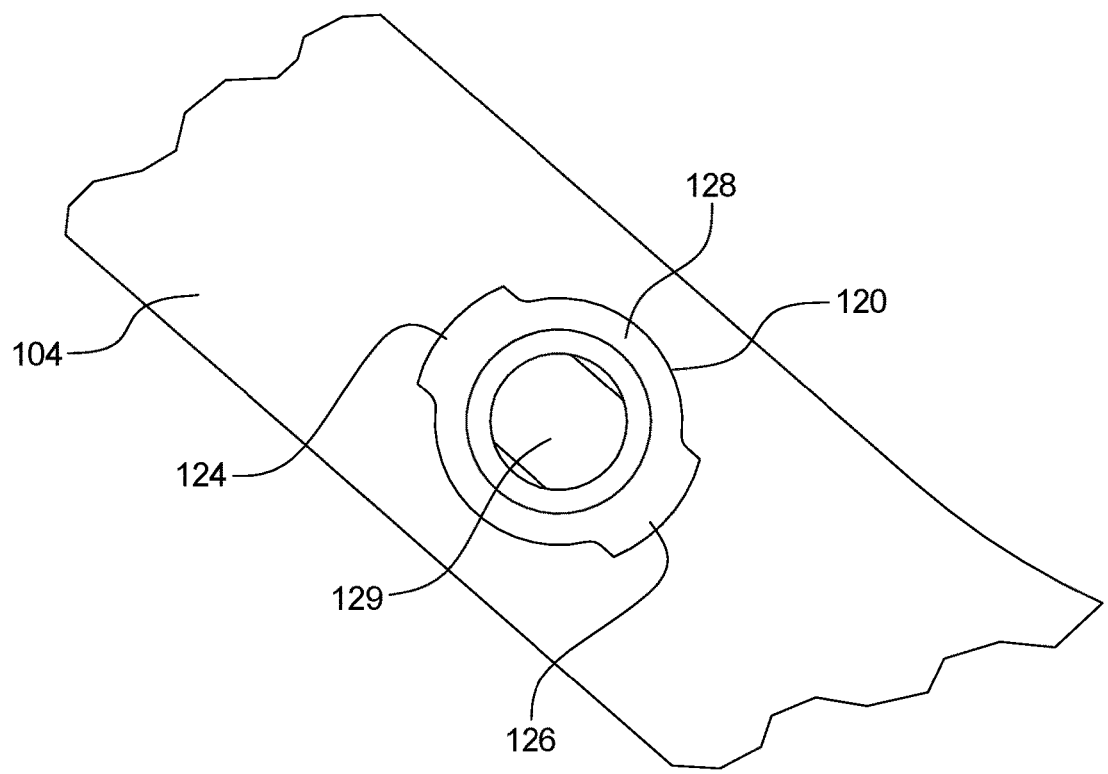
FIG. 6 is a perspective view of a port of the bone graft dispensing device.
Figure 10:
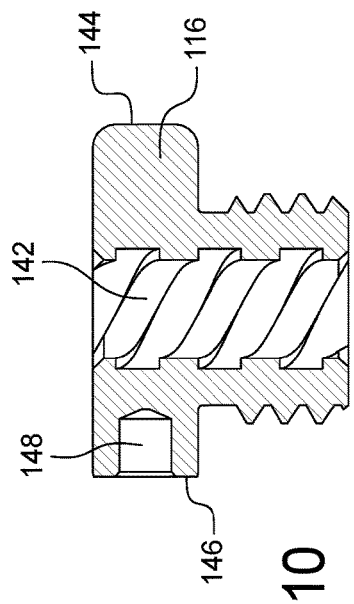
FIG. 10 is a sectional view of the cap.
Figure 11:
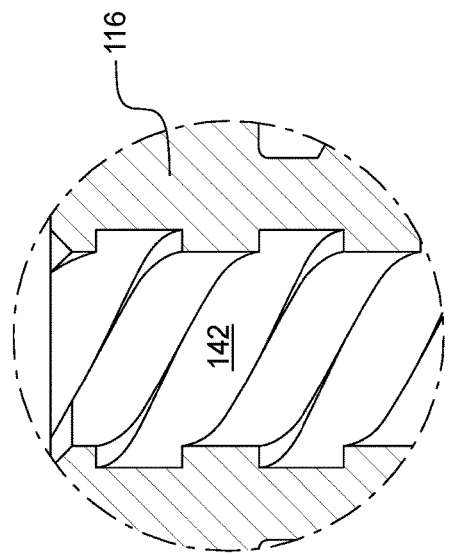
FIG. 11 is an expanded view of FIG. 10.
Figure 7:
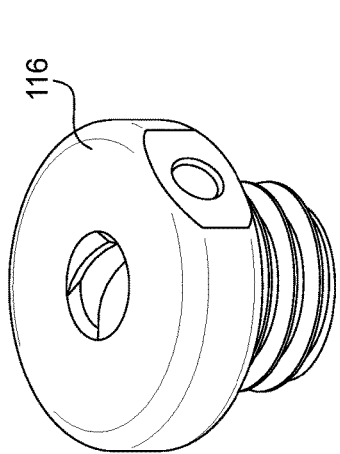
FIG. 7 is a perspective view of an example of the cap of the bone dispensing device.
Figure 8:
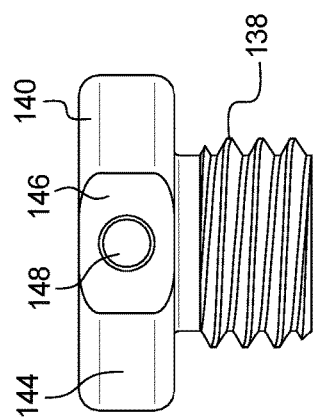
FIGS. 8 and 9 are side elevational and plan views of the cap.
Figure 9:
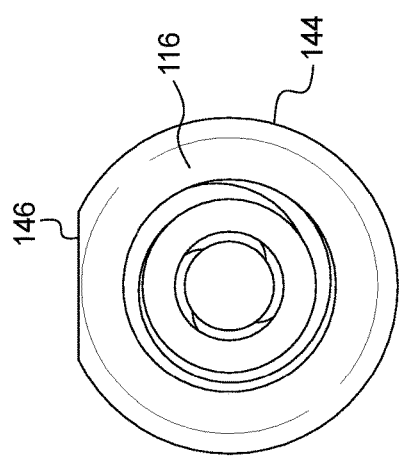

As shown in FIG. 3, an attachable insert 200 can attach to funnel 106 to aid in adding the bone graft material into funnel 106. The attachable insert can be in the shape of a cylinder or funnel. Once the bone graft material is added into the funnel 106 via the attachable insert 200, the attachable insert 200 can be removed. In an example, a loading plunger can be attached to funnel 106 to move the bone graft material from funnel 106 into the cylinder 104. Alternatively, or in addition to, the attachable insert 200 can be removed and a handle can be attached to funnel 106 to deliver the bone graft material.

The plunger can be a threaded graft impactor that rotates through the handle to advance the bone graft material. As a distal end of the plunger is threaded into the cylinder, the proximal end of the plunger includes an adapter that may cooperate with a handle or a powered drill. The plunger may be made of metal, a high-strength plastic, or other suitable material. The cylinder is made of a clear, radiolucent material such as plastic.

In one example, the cylinder can have an outer diameter of about 8 to about 12 mm and an inner diameter of about 6 to about 8 mm. In another embodiment, the length of the cylinder may be about 20 cm, and the volume may be about 8 cc. In some embodiments, the cylinder is marked to show volume.

Figure 2:
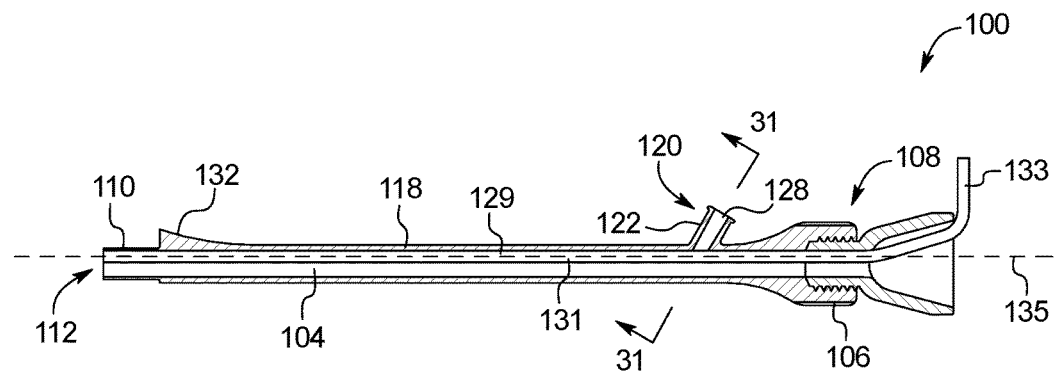
FIG. 2 is a perspective view of the bone graft dispensing device of FIG. 1 including a sleeve.

As shown in FIGS. 1-3, the cylinder 104 includes a body 118 extending between the proximal and distal ends 108, 112. A port 120 can extend from the body 118 near the proximal end 108 spaced from the funnel 106, wherein the port 120 is configured to receive a conventional syringe (not shown) or other suitable device. Specifically, the port 120 includes a port body 122 integrally formed with and extending outwardly at an angle from the central axis 135 of the bone dispensing device 100. The interior of the port 120 is in fluid communication with the interior of the cylinder.

As seen in FIGS. 2-3, first and second opposing ridges 124, 126 extend outwardly along a mouth 128 of the port 120 and engage with the syringe to hold the syringe in place. During use, a syringe may be secured to the port 122 in order to load a liquid into the bone graft dispensing device 100 for hydrating the bone graft material. Example liquids that can be added via the port 122 can include saline, blood, bone marrow aspirate, or any other suitable hydrating liquid.

A removable sleeve 129 may optionally be positioned within the cylinder 104 before the bone graft material is loaded into the device 100 such that removal of the sleeve 129 creates a channel within the loaded bone graft material. The liquid can then be injected into the port 120 to fill the channel within the loaded bone graft material. In an example, the port 120 is in fluid communication with the channel created by the removal of the sleeve 129.

Specifically, before the bone graft material is added into the cylinder, the sleeve 129 may be positioned within the cylinder 104 between the proximal end of 108 and/or the port 122 and the distal end 112 and aligned with the port 122. Once the bone graft material is loaded into the cylinder 104, the sleeve 129 can be removed to form the channel. The syringe may then be secured to the port 120 and used to inject liquid into the cylinder 104. In an example, the injected liquid fills the channel formed by the removal of the sleeve 129.

In an example, the sleeve 129 can include a sleeve body 131 with a handle portion 133 that the user can manipulate as the bone graft material is being loaded into the device 100 to ensure that the channel will be aligned with the port 120. The handle portion 133 may be formed integrally with the sleeve body 131 or separately and attached to the sleeve body 131.

In an example, the sleeve 129 is positioned between the distal end 112 and the proximal end 108, wherein the sleeve extends out of the proximal end and/or out of the funnel 106. In another example, the sleeve 129 extends from the distal end 112 to and out of the port 120. After the bone graft material is added to the cylinder, via the funnel 106, the hydrating liquid can be added into the sleeve. After which, the sleeve 129 can be removed, leaving the liquid in the cylinder within the bone graft material. Alternatively, or in addition to, after the bone graft material is added to the cylinder, via the funnel 106, the sleeve 129 can be removed, forming a channel within the bone graft material. After which, the liquid can be added into the channel via the port 120, to dispense the liquid into the bone graft material. In an example, the sleeve can extend out of the proximal end of the cylinder.

In an example, the sleeve body 131 comprises a guide wire. In an example, the guide wire can have a diameter of about 3.2 mm having a length with a centerline 135. In other embodiments, the sleeve body 131 may be cylindrical, square, rectangular triangular, or any other suitable shape in cross section. The handle portion 133 may be a length of the sleeve body 131 that extends away from a centerline 135 of the sleeve body 131. Alternatively, the handle portion 133 may include a flattened surface for handling.

While the sleeve 129 can be provided with the present bone graft dispensing device 100, the sleeve 129 may be designed and/or used with any bone graft dispensing device or any device that may utilize a channel to hydrate material loaded into a similar device.

Referring to FIG. 3, the funnel 106 at the proximal end 108 of the cylinder 104 can include an inner threaded surface 130 that engages with the cap 116. Near the distal end 112, a protrusion 132 extends outwardly from the central axis 135 of the cylinder 104 adjacent the tip 110. The protrusion 132 can include a planar surface 134 transverse to the central axis 135 and a sloped surface 136 parallel to the central axis 135. The width of the protrusion 132 can be slightly less than the diameter of the cylinder 104. In an example, the geometry of the surfaces and dimensions of the protrusion may vary depending on the application, the manufacturing requirements, or any other factors.

Shown in FIGS. 7-11, the cap 116 includes a threaded body 138 extending from a cover 140. The threaded body 138 of the cap 116 engages with the inner threaded surface 130 of the funnel 106 of the cylinder 104. A threaded bore 142 runs through the cap 116 along the central axis 135 to receive the plunger 102. A handle 114 is secured to a cap 116 that encloses the funnel 106 of the cylinder 104. In an example, the handle 114 and cap 116 are one piece. FIGS. 7-11 illustrate the perimeter of the cover 140 including a rounded portion 144 with a smaller planar portion 146 with an opening 148 that receives the handle 114.

Figure 12:
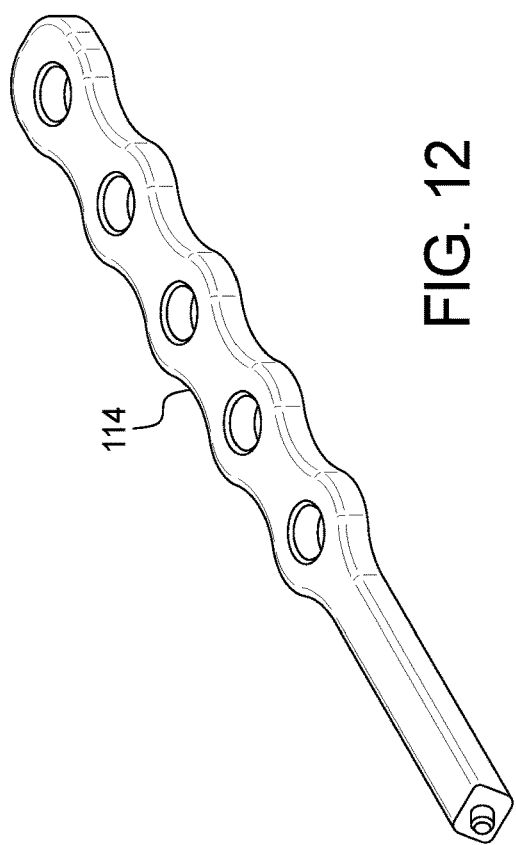
FIG. 12 is a perspective view of the handle of the bone dispensing device of FIG. 1.
Figure 13:
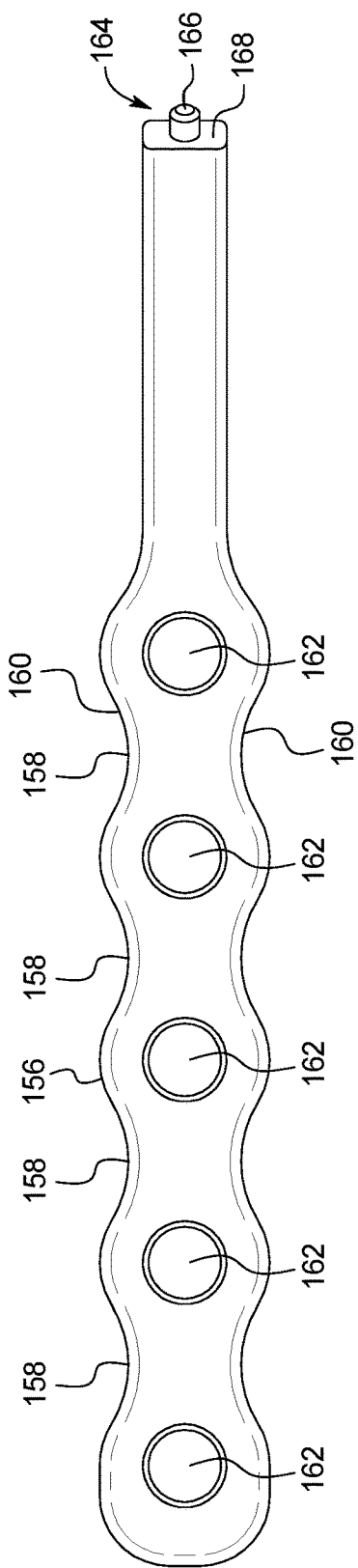
FIG. 13 is a top view of the handle.

FIGS. 12-13 illustrate the handle 114 of the bone graft dispensing device 100. The relatively planar handle 114 includes an upper surface 150 and a lower surface 152 spaced apart by a thickness 154. A gripping portion 156 of the handle 114 includes indentations 158 along the outer surfaces 160 that enable the user to easily grasp the handle 114. A plurality of openings 162 within the gripping portion 156 are offset from the indentations 158.

At a connecting end 164 opposite of the gripping portion 156, a protrusion 166 extending outwardly from a planar surface 168 along the thickness 154 of the handle 114. The planar surface 168 is angled relative to the upper and lower surfaces 150, 152 of the handle 114. As shown in FIGS. 14-16, the protrusion 166 on the connecting end 164 of the handle 114 engages with the opening 148 in the perimeter of the cover 144 of the cap 116 during use. The handle 114 extends at an angle from the centerline 105 of the bone graft dispensing device 100. The handle can be used to control, handle, and/or stabilize the device while the bone graft material is implanted into the patient.

The plunger 102 can be a threaded graft impactor that rotates through the cap 116 and cylinder 104 to advance the bone graft material through the bone graft dispensing device 100. A proximal end 170 of the plunger 102 includes a planar surface 172 that may cooperate with a manual or powered drill. A distal end 174 of the plunger 102 has a flat, planar surface 176 that contacts the bone graft material during use. The plunger 102 may be made of metal, plastic, or other suitable material.

A threaded plunger offers a controlled advancement of the bone graft material into the patient. Specifically, a threaded plunger allows a mechanical advantage of controlled greater mechanical force to advance the bone graft material. Conventional plunger systems can require the use of a mallet on a traditional funnel that could potentially plunge into the patient and damage a patient's spinal cord.

The cylinder 104 can be made of a clear, radiolucent material such as plastic. In some embodiments, the cylinder 104 is marked to show volume. In one example, the cylinder 104 has an outer diameter of about 8 to about 12 mm and an inner diameter of about 6 to about 8 mm. The length of the cylinder 104 can be about 20 cm. The inner and outer diameters and the volume may vary based on the application and/or preference.

It should be noted that various changes and modifications to the presently preferred embodiments described herein will be apparent to those skilled in the art. Such changes and modifications may be made without departing from the spirit and scope of the present invention and without diminishing its attendant advantages.

The invention claimed is:

1. A method for dispensing bone graft material, the method comprising:
    providing a bone graft dispensing device including
        a cylinder including a funnel at a proximal end and a dispensing tip at a distal end, and
        a removable sleeve positioned within the cylinder;
    adding a bone graft material into the cylinder via the funnel;
    removing the removable sleeve from the cylinder, wherein the removal of the sleeve forms a channel within the bone graft material;
    adding a hydrating fluid into the channel to form a hydrated bone graft material;
    positioning a plunger within an interior of the cylinder, wherein the plunger is positioned within an opening in a cap, wherein the cap is positioned within the funnel of the cylinder, wherein the plunger is movable along a central axis within the interior of the cylinder, wherein the cap includes a cylindrical opening; and
    depressing the plunger through the cylinder toward the distal end of the cylinder, wherein the depression of the plunger releases the hydrated bone graft material through the dispensing tip.

2. The method of claim 1, wherein the cylinder includes a protrusion extending outwardly from the central axis adjacent to the distal end.

3. The method of claim 1, wherein the cylinder includes a port extending outwardly from the central axis, wherein the hydrating fluid is added to the channel via the port, wherein the port is in fluid communication with the interior of the cylinder.

4. The method of claim 1, wherein the cap is threadably engaged with an interior of the funnel of the cylinder.

5. The method of claim 1, further comprising a port extending outwardly from the central axis, wherein the port is in fluid communication with the interior of the cylinder, wherein the removable sleeve is positioned within the cylinder and extends out of the port.

6. The method of claim 1, further comprising a handle extending from the cap.

* * * * *